(12) United States Patent
Müller et al.

(10) Patent No.: US 11,213,403 B2
(45) Date of Patent: Jan. 4, 2022

(54) DEVICES AND METHODS FOR OPTIMIZED SPINAL FIXATION

(71) Applicant: Medos International Sari, Le Locle (CH)

(72) Inventors: Marc Müller, Weil am Rhein (DE); Thomas McCann, Jr., Limerick, PA (US); Luke Ice, Garret, IN (US); William Miller, Middleboro, MA (US)

(73) Assignee: Medos International Sarl, Le Locle (CH)

( * ) Notice: Subject to any disclaimer, the term of this patent is extended or adjusted under 35 U.S.C. 154(b) by 182 days.

(21) Appl. No.: 16/353,476

(22) Filed: Mar. 14, 2019

(65) Prior Publication Data

US 2020/0289288 A1    Sep. 17, 2020

(51) Int. Cl.
  *A61F 2/44*   (2006.01)
  *A61F 2/30*   (2006.01)
  *A61F 2/46*   (2006.01)

(52) U.S. Cl.
  CPC ........ *A61F 2/4465* (2013.01); *A61F 2/30749* (2013.01); *A61F 2/4611* (2013.01); *A61F 2002/30056* (2013.01); *A61F 2002/30092* (2013.01); *A61F 2002/3093* (2013.01); *A61F 2002/30322* (2013.01); *A61F 2002/30593* (2013.01); *A61F 2002/30622* (2013.01);
  (Continued)

(58) Field of Classification Search
  CPC .................................................. A61F 2/4465
  See application file for complete search history.

(56) References Cited

U.S. PATENT DOCUMENTS 5,306,309 A * 4/1994 Wagner ................... A61L 27/10
                                                             623/17.16
7,270,679 B2   9/2007 Istephanous et al.
(Continued)

FOREIGN PATENT DOCUMENTS

EP        2727559 A1    5/2014
WO    2017001851 A1    1/2017
(Continued)

OTHER PUBLICATIONS

International Search Report and Written Opinion for Application No. PCT/EP2020/056333, dated Jul. 2, 2020 (11 pages).

*Primary Examiner* — Nicholas W Woodall
(74) *Attorney, Agent, or Firm* — Barnes & Thornburg LLP (57) ABSTRACT

Devices and methods are provided for optimized spinal fixation using additive manufacturing techniques to create implants with optimized structure for various surgical approaches, anatomies, etc. One exemplary embodiment includes a cage having an X-shaped connection that can bear a load during cage impaction. The cage can be additively manufactured to incorporate features such as variable wall thickness or material density to adjust properties of the cage, including load bearing capability, flexibility, radiolucency, etc. The cage can further include one or more of the connectors disposed between upper and lower endplates. In some embodiments, the cage can include a feature for coupling an insertion device thereto for introducing the cage into the body of a patient. In some embodiments, a plate can be appended to or integrally formed with a proximal end of the cage to assist with securing the cage to vertebral bodies.

20 Claims, 7 Drawing Sheets

(52) U.S. Cl.
CPC ............... *A61F 2002/30677* (2013.01); *A61F 2002/30784* (2013.01); *A61F 2002/30948* (2013.01); *A61F 2002/30985* (2013.01); *A61F 2002/4658* (2013.01); *A61F 2310/00023* (2013.01); *A61F 2310/00179* (2013.01)

(56) References Cited

U.S. PATENT DOCUMENTS

| | | | |
|---|---|---|---|
| 7,666,522 | B2 | 2/2010 | Justin et al. |
| 8,133,421 | B2 | 3/2012 | Boyce et al. |
| 8,147,861 | B2 | 4/2012 | Jones et al. |
| 9,205,176 | B2 | 12/2015 | Hunter et al. |
| 9,433,707 | B2 | 9/2016 | Swords et al. |
| 9,636,229 | B2 | 5/2017 | Lang et al. |
| 9,775,711 | B2 | 10/2017 | Li et al. |
| 9,788,951 | B2 | 10/2017 | Coale et al. |
| 9,849,019 | B2 | 12/2017 | Miller et al. |
| 9,867,903 | B2 | 1/2018 | Jin et al. |
| 9,883,953 | B1 | 2/2018 | To et al. |
| 9,918,849 | B2 | 3/2018 | Morris et al. |
| 9,943,378 | B2 | 4/2018 | Kieser |
| 9,962,269 | B2 | 5/2018 | Jones et al. |
| 9,993,341 | B2 | 6/2018 | Vanasse et al. |
| 10,531,962 | B2 * | 1/2020 | Petersheim ............ A61F 2/4455 |
| 2006/0129240 | A1 | 6/2006 | Lessar et al. |
| 2010/0137990 | A1 | 6/2010 | Apatsidis et al. |
| 2011/0190888 | A1 * | 8/2011 | Bertele ..................... A61F 2/46 623/17.11 |
| 2014/0249643 | A1 | 9/2014 | Jones et al. |
| 2015/0093283 | A1 | 4/2015 | Miller et al. |
| 2015/0134063 | A1 | 5/2015 | Steinmann et al. |
| 2015/0335434 | A1 | 11/2015 | Patterson et al. |
| 2016/0128843 | A1 | 5/2016 | Tsau et al. |
| 2016/0136728 | A1 | 5/2016 | Srivas et al. |
| 2016/0199193 | A1 | 7/2016 | Willis et al. |
| 2017/0020571 | A1 | 1/2017 | Hawkes et al. |
| 2017/0156878 | A1 | 6/2017 | Tsai et al. |
| 2017/0183231 | A1 | 6/2017 | Morris |
| 2017/0239064 | A1 | 8/2017 | Cordaro |
| 2018/0042646 | A1 | 2/2018 | Frey et al. |
| 2018/0071113 | A1 | 3/2018 | Melkent et al. |
| 2018/0104063 | A1 | 4/2018 | Asaad |
| 2018/0110624 | A1 | 4/2018 | Arnone |
| 2018/0110627 | A1 | 4/2018 | Sack |

FOREIGN PATENT DOCUMENTS

| | | |
|---|---|---|
| WO | 2017087927 A1 | 5/2017 |
| WO | 2017087944 A1 | 5/2017 |
| WO | 2017091657 A1 | 6/2017 |
| WO | 2018017369 A2 | 1/2018 |
| WO | 2018026449 A1 | 2/2018 |
| WO | 2018026902 A1 | 2/2018 |
| WO | 2018055359 A1 | 3/2018 |

* cited by examiner

DEVICES AND METHODS FOR OPTIMIZED SPINAL FIXATION

FIELD

The present disclosure relates to devices and methods for optimizing spinal fixation and stability, and more particularly relates to devices for and methods of improving spinal fusion rates by using additive manufacturing to create optimized implants configured for insertion into various locations of a subject's body.

BACKGROUND

The human spine includes vertebrae and joints that work together to protect the spinal cord from injury during motion and activity. The spinal cord generally includes nerve elements that travel from the brain to other portions of the body so that the brain can command the other portions of the body to respond in particular manners based on bioelectrical and biochemical signals transmitted by the brain, through the spinal cord, and ultimately to the portion of the body being commanded by the brain. In the event of deformity, injury, and other spinal abnormalities, implants and other instruments are often inserted into the spine to coerce the spine into proper alignment and ease tension on the surrounding nerves to alleviate pain. These implants aim to strengthen the body's ability to avoid further injury while assisting the body to work to repair the injury using the body's own healing techniques.

Existing implants and methods for treating and correcting spinal problems have several shortcomings. After implants are inserted into the spine, a variety of factors can contribute to low spinal fusion rates, which can result in patient complications. For example, mass production of implants can fail to take into account the differences between the cervical, thoracic, lumbar, and sacral spine, as well as the variations in vertebral levels that occur between patients of different ages and sizes. As a result, implant migration can occur, which may slow healing time or require corrective surgery to repair. Further, misalignment between the implant and certain areas of the spine can cause further damage by improperly distributing impaction forces over the spine. Still further, inserted implants may not be sufficiently elastic or otherwise strong so as to allow the implants to withstand forces exerted thereon by spinal structures, causing unwanted deformation or breaking that may require further corrective surgery.

Accordingly, it would be desirable to provide devices and methods that can be used for treatment and/or fixation of spinal structures that can be optimized for the anatomical geometry and needs of a subject.

SUMMARY

In one aspect, a spinal implant is provided that can include an upper plate, a lower plate, a tapered end extending between the upper plate and the lower plate that is configured for insertion into intervertebral space, a second end opposite the tapered end; and a plurality of struts extending laterally between the tapered end and the second end.

The devices and methods described herein can have a number of additional features and/or variations, all of which are within the scope of the present disclosure. In some embodiments, for example, the spinal implant can include a connector extending between the upper plate and the lower plate. Further, the connector can be disposed within an interior volume defined by the implant.

In certain embodiments, the spinal implant can include a connector extending between any of the upper plate and the lower plate and one or more of the plurality of struts. And in some embodiments, the connector can be formed along a perimeter wall of the implant. Further, in some embodiments, the spinal implant can include a connector configured to support loads applied to the upper end plate and the lower end plate.

In certain embodiments, the connector can define a hollow inner lumen. And in some embodiments, the connector can be formed of a porous mesh. Further, in some embodiments, at least a portion of the implant is formed of a porous mesh or lattice structure configured to promote osteointegration. And in some embodiments, the portion of the implant can be formed of any of titanium, polyetherketoneketone (PEKK), a ceramic, and a nickel titanium alloy (e.g., Nitinol).

In certain embodiments, any of the upper plate and the lower plate can be curved such that a distance between the upper plate and the lower plate varies along the implant. And in some embodiments, any of the upper plate and the lower plate can be curved such that a distance between the upper plate and the lower plate varies along the implant. Further, in some embodiments, at least one of the upper plate and the lower plate can include a roughened surface configured to promote bone fusion. Still further, in some embodiments, the implant can be formed of a porous titanium mesh having reduced stiffness and increased radiolucency compared to solid titanium. And in some embodiments, at least one of the upper plate and lower plate can include one or more surface features configured to prevent migration of the implant.

In certain embodiments, at least two of the plurality of struts can cross to form an X-shaped connection extending along a sidewall of the implant between the upper plate, lower plate, tapered end, and second end.

In some embodiments, an orifice can be formed in the second end of the implant. Further, in some embodiments, the spinal implant can include a plate having a plurality of through-holes being coupled to the second end of the implant. And in other embodiments, the spinal implant can include a plate having a plurality of through-holes that is integrally formed with the second end of the implant. In some embodiments, one of the plurality of through-holes in the plate can align with the orifice formed in the second end of the implant. Further, in some of the embodiments, one of the plurality of through-holes can be disposed in any of above the upper plate or below the lower plate. Still further, the plate can couple to the implant by interfacing with surface features formed on first and second sidewalls of the second end of the implant that are disposed on opposite sides of the orifice.

In another aspect, a method for spinal fixation is provided that can include determining characteristics of an intervertebral space of a patient, additively manufacturing a spinal implant based on the determined characteristics of the intervertebral space, the spinal implant being defined by an upper plate, a lower plate, a tapered end extending between the upper plate and the lower plate, a second end opposite the tapered end, and a plurality of struts extending laterally between the tapered end and the second end, and inserting the spinal implant into the intervertebral space.

As with the above-described aspect, a number of additional features and/or variations can be included, all of which are within the scope of the present disclosure. In some embodiments, for example, characteristics of the intervertebral space can include curvature of adjacent vertebrae and additively manufacturing the spinal implant includes forming at least one of the upper and lower plates with curvature that matches the curvature of the adjacent vertebrae. Further, additively manufacturing a spinal implant based on the determined characteristics of the intervertebral space can include shaping one or more struts to form a wall of the spinal implant extending from the tapered end to the second end. Still further, a plurality of struts can be shaped into an X-shaped pattern to form the wall of the spinal implant extending from the tapered end to the second end.

In certain embodiments, determining the characteristics of the intervertebral space can include imaging the intervertebral space with any of MRI, CT, ultrasound, or optical imagers. And in some embodiments, additively manufacturing a spinal implant based on the determined characteristics of the intervertebral space can include reducing a density of material used to form the implant based on any of desired stiffness and strength. Further, in certain embodiments, the material used to form the implant can be any of titanium, polyetherketoneketone (PEKK), a ceramic, and a nickel titanium alloy.

In some embodiments, the method for spinal fixation can include coupling a plate member to the spinal implant to secure the spinal implant to at least one adjacent vertebra using one or more bone anchors. In some embodiments, the method for spinal fixation can include securing the spinal implant to at least one adjacent vertebra using one or more bone anchors inserted through a plate member that is integrally formed with the spinal implant. Further, in some embodiments, the plate member can be secured to both vertebrae adjacent the spinal implant. Still further, in some embodiments, the method for spinal fixation can include delivering bone growth-promoting materials into an interior of the spinal implant to enhance and expedite integration of the implant into a subject's body.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Devices and methods for improving spinal fusion by fixing and/or stabilizing a location of bones in the spine are generally provided. In particular, the devices and methods disclosed herein allow for adjustment and optimization of an implant by using additive manufacturing to form the implant, e.g., a fusion cage, based on particular characteristics of the patient and anatomy. Additive manufacturing generally refers to manufacturing a part by adding material as opposed to subtracting, and thus is a way by which parts can be printed three-dimensionally. Additive manufacturing is growing in popularity because it allows users to create unique geometries and process unique material compositions. Implants can be additively manufactured to vary the design of the implant based on delivery of the implants. For example, the design of spinal implants for delivery from a lateral point of access can differ from implants inserted from a posterior-lateral location. By additively manufacturing the implants, the implants can be adjusted to add or remove material based on access point, area of implantation, anatomy of the patient, and so forth. For example, in some embodiments, material can be added to increase a load capability of an implant having a small footprint, or excess material can be removed from the implant to allow for more space in and/or around the implant for introduction of bone material, as well as to adjust characteristics of the implant, such as flexibility, radiolucency, etc. The ability to add and/or remove material from the implant can allow a single implant to be delivered through various access points into multiple areas of the spine without compromising the integrity of the implant or having to manufacture multiple implants, thereby greatly reducing costs of the procedure. Removing excess material from the implant can produce a radiolucent, low-density implant that can allow for post-operative evaluation of fusion. While the density of the implant can vary, optimizing the density of the implant to a value that is less than that of, e.g., a solid titanium cage can facilitate manipulation of the cage when aligning the curvature of the cage with upper and lower vertebral surfaces. Removing excess material can also reduce a weight of an implant having a larger footprint.

A variety of devices and methods are disclosed herein. Some devices include spinal implants configured to be disposed between adjacent vertebrae. Other devices include spinal fixation elements that can be configured to extend from one vertebra to one or more additional vertebrae, even if those vertebrae are not adjacent. The methods include surgical techniques that allow implants to be disposed through a small incision that is positioned laterally, anteriorly, or posterior-laterally on a subject being treated. In the present disclosure, like-numbered components of the embodiments generally have similar features, and thus within a particular embodiment each feature of each like-numbered component is not necessarily fully elaborated upon. Further, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Sizes and shapes of each of devices, and the components thereof, can depend at least on the anatomy of the subject in which the devices will be used and the size and shape of components with which the devices will be used.

Figure 1:
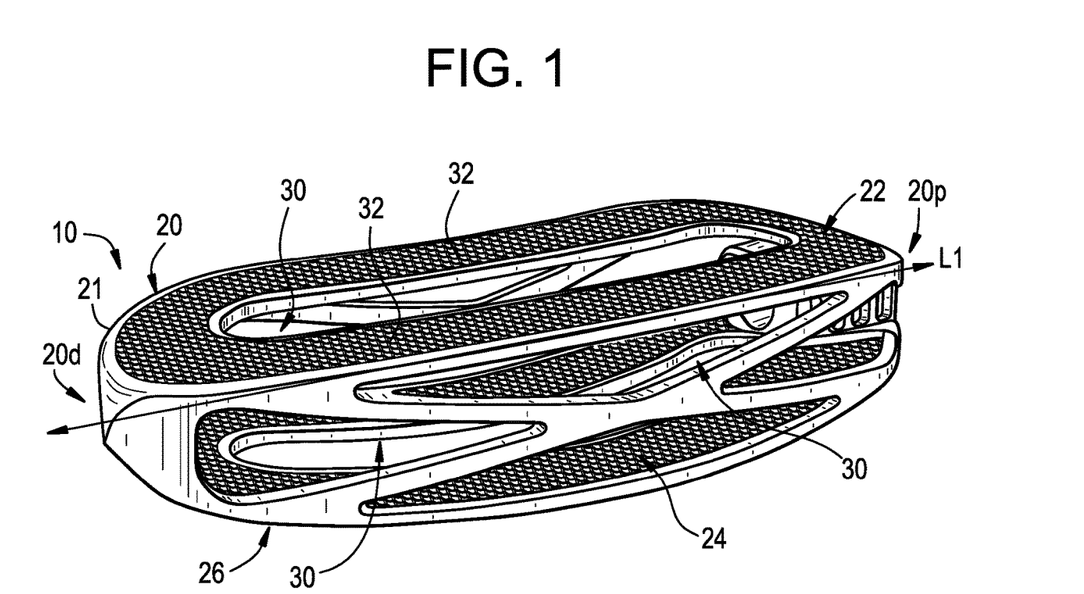
FIG. 1 is a perspective view of one exemplary embodiment of a spinal implant that includes a cage.

FIG. 1 illustrates one embodiment of a spinal implant 10, which is in the form of a lateral fusion cage 20 that can have a generally rectangular, oval, or kidney shape. As explained below, although the disclosed embodiments of the cages have a lateral design that lend themselves to implantation in a subject's spine via a lateral or posterior-lateral surgical approach, the design can be altered to facilitate TLIF, ALIF, or cervical approaches. Moreover, the design can be such that the implant maximizes the footprint of the implant that resides between adjacent vertebral bodies while providing a large internal volume, which can serve as a graft chamber for bone graft-inducing material. Maximization of the footprint of the implant can be optimized based on the desired site of implantation, the anticipated bearing load, and other parameters recognized by one skilled in the art to provide stability while also using minimal amounts of material that still achieve peak performance.

Utilizing additive manufacturing of the cage 20 can allow optimization of several cage parameters. For example, cage stiffness can be varied by altering the design of the cage. Further, the implant can be made from any number of biologically-compatible materials used to form spinal implants, including materials that are partially or fully bioresorbable. Exemplary materials include titanium, titanium alloys, polyether ether ketone (PEEK), reinforced PEEK, polyetherketoneketone (PEKK), nickel titanium alloys such as Nitinol, and ceramics. It will be appreciated that PEEK cages can have a stiffness that is similar to that of bone. Although titanium typically has higher stiffness than PEEK cages, altering the design of the cage, as described below, can lower the stiffness of the cage such that it is better adapted to that of bone. Cages having a stiffness that is similar to vertebral bone can be particularly suited to promoting fusion and avoiding subsidence. In some embodiments, the stiffness of the cage can range from approximately 5,000 N/mm to approximately 25,000 N/mm, from approximately 7,000 N/mm to approximately 17,000 N/mm, from approximately 10,000 N/mm to approximately 15,000 N/mm, or be approximately 12,000 N/mm. In some embodiments, titanium mesh can be used as a surface feature. In some embodiments, one or more portions of the cage can be formed from ceramics. Ceramic materials can be degradable and can have superior integration properties as compared to titanium or PEEK.

The cage 20 can have an external surface 21 that extends between the proximal and distal ends 20$p$, 20$d$, which can be defined by an upper endplate 22, a lower endplate 24, an anterior wall 26, and a posterior wall 28. As shown, the cage 20 can be elongate, and for reference purposes can be described as being oriented along a longitudinal axis $L_1$ in the transverse plane. One or more graft windows or openings 30 can be formed in the external surface 21 to permit access to an internal volume within the cage 20. The internal volume of the cage 10 may be packed with bone graft and/or bone growth-promoting materials to enhance and expedite integration of the implant into a subject's body. In the illustrated embodiment of FIGS. 1 and 2, each of the upper endplate 22, lower endplate 24, anterior wall 26, and posterior wall 28 includes openings 30. In other embodiments, however, only some of the surfaces or walls may include an opening(s), or even none of the surfaces or walls may include openings. Similarly, more than one opening can be formed on one or more sides of the external surface 21.

Figure 2:
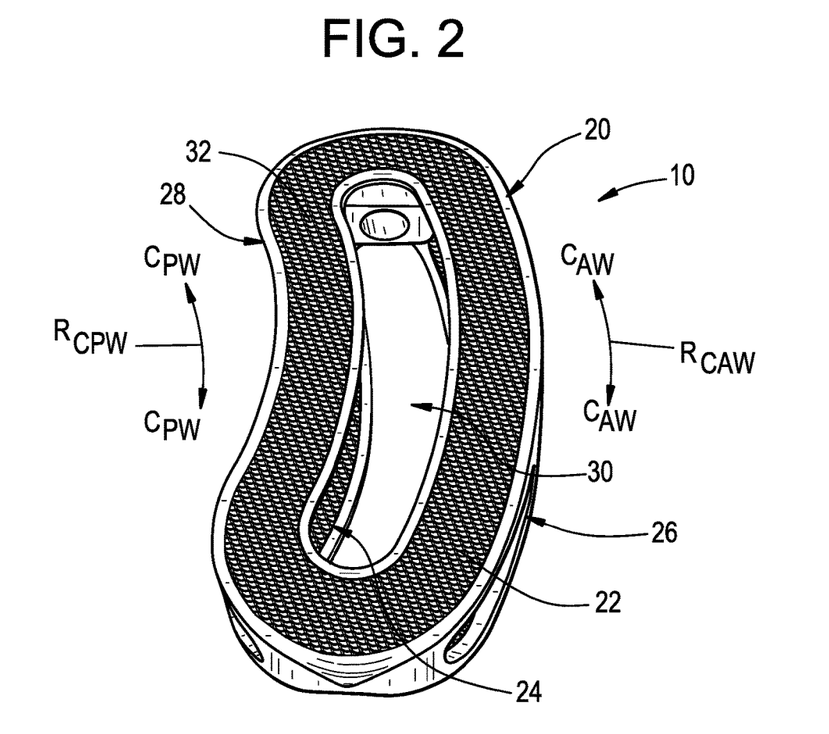
FIG. 2 is a perspective top view of the cage of FIG. 1.

The surfaces 22, 24, 26, and 28 that define the external surface 21 of the cage are sized and shaped in a manner that optimizes the placement and fixation of the cage 20 between vertebral bodies in the spine, and particularly when the implant is positioned within the spine through lateral or posterior-lateral access. As shown in FIG. 2, the surfaces 22, 24, 26, and 28 are configured to be complementary to the shape of the vertebral bodies at the site of implantation. For example, the anterior wall 26 can be curved and can be configured to be disposed at or proximate to an anterior portion of the vertebral body, while the posterior wall 28 can also be curved and can be configured to be disposed at or proximate to a posterior portion of the vertebral body. As illustrated, a curve $C_{AW}$ the anterior wall 26 can be generally convex while a curve $C_{PW}$ of the posterior wall 28 can be generally concave. Radii $R_{CAW}$, $R_{CPW}$ of the curves $C_{AW}$, $C_{PW}$ can vary depending on the size of the implant and the location at which the measurement is taken. In some embodiments, the radii $R_{CAW}$, $R_{CPW}$ can be substantially the same and in other embodiments can be different, and the radii can be in the range of about 5 millimeters to about 55 millimeters. In some embodiments, such as the lumbar cage shown in FIG. 2, the radii $R_{CAW}$, $R_{CPW}$ can be between about 30 millimeters and 50 millimeters. More specifically, in the illustrated embodiment of FIG. 2, the radius $R_{CAW}$ is about 50 millimeters and the inner radius $R_{CPW}$ is about 30 millimeters. In some embodiments, e.g., in smaller cervical cages, the range of the radii $R_{CAW}$, $R_{CPW}$ can be between about 10 millimeters and about 30 millimeters.

Figure 4A:
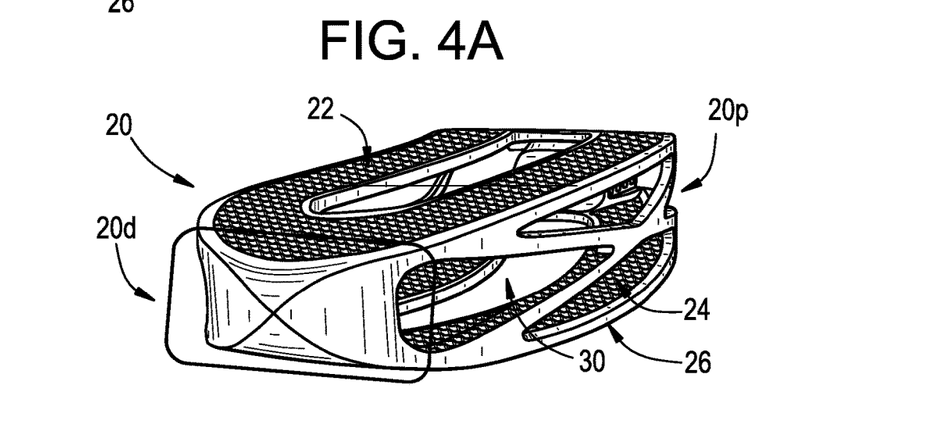
FIG. 4A is a perspective side view of a distal end of the cage of FIG. 1.
Figure 4B:
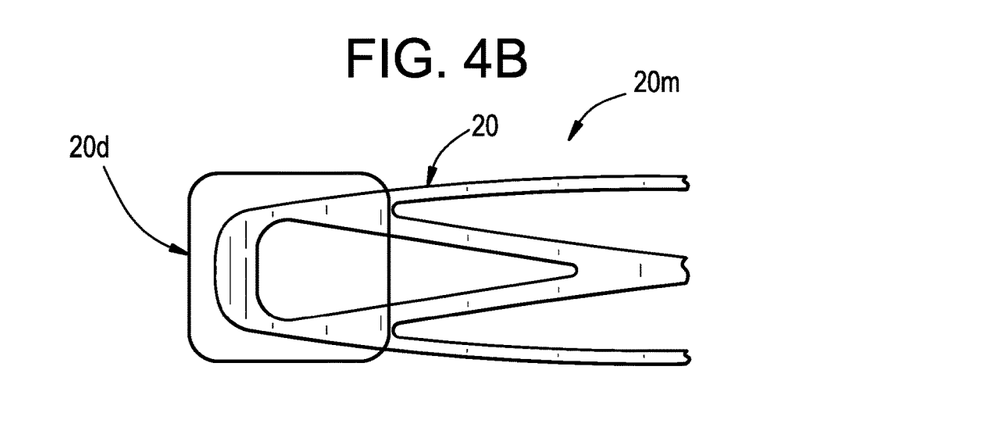
FIG. 4B is a side view of the distal end of the cage of FIG. 1.

The cage can be regarded to be of a generally rectangular shape in that it is elongate and has four sides. However, as explained below, each of the sides can be non-linear in shape. For example, as shown in FIG. 4, the cage 20 can have a tapered distal end 20$d$ (e.g., curved or having converging walls of various geometries) and the cage can generally be described as having a generally kidney-like, banana-like, or canoe-like shape to assist with positioning of the cage upon introduction into the disc space. In some embodiments, the cage 20 can include a pointed distal end 20$d$, while in other embodiments the cage can include an asymmetrically-curved, bullet-shaped distal end 20$d$. Any of a variety of other tapering profiles can also be utilized to form the distal end 20$d$ of the cage 20. Further, one having ordinary skill in the art will appreciate that particular curvatures of the cage can be advantageous in certain instances, although a variety of other shapes and curves can also be used in such spinal fixation techniques without departing from the spirit of the invention. Accordingly, although certain embodiments of the cage 20 are described as having walls and surfaces that are convex or concave, any walls and surfaces of the cage can be virtually any shape, including generally flat, convex, or concave. Likewise, the cage can take the form of a variety of other shapes.

Figure 3:
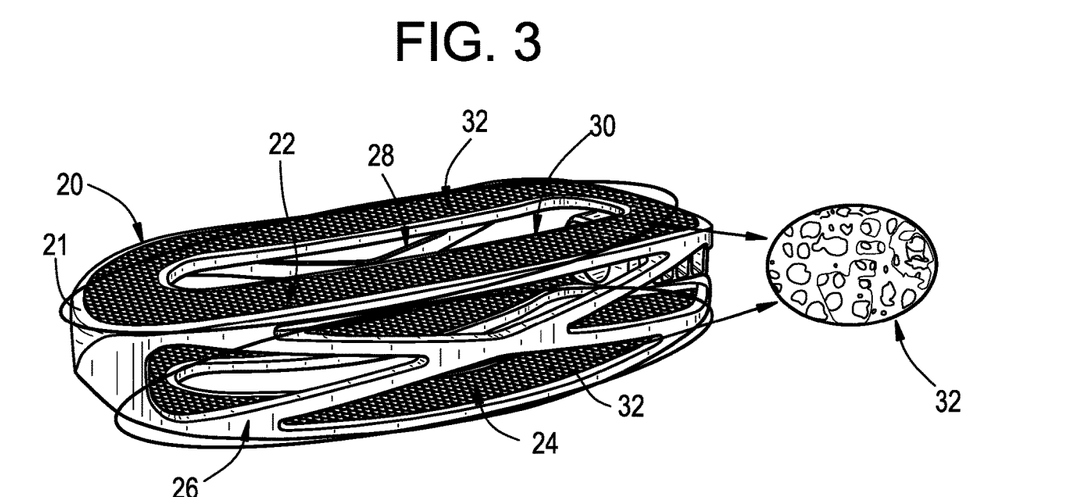
FIG. 3 is a perspective view of the cage of FIG. 1 highlighting a porous upper endplate and a porous lower endplate.

The external surface 21 of the cage 20 may include surface features that prevent migration and assist in maintaining a location of the spinal implant. For example, in the illustrated embodiments, one or more of the upper and lower endplates 22, 24 can include a wire, a lattice structure, or mesh 32 extending along a surface thereof. As shown in FIG. 3, the mesh 32 can extend along the upper and lower endplates 22, 24 around the circumference of the openings 30 to facilitate transfer of the bone growth-promoting material through the endplates 22, 24 into and/or out of the cage 20. A pore diameter of the mesh 32 can vary, but one skilled in the art will appreciate that the mesh 32 should be sufficiently porous to promote improved bone formation inside the cage 20. For example, a porosity of the mesh can be approximately 50%, approximately 55%, approximately 60%, approximately 65%, approximately 70%, approximately 75%, approximately 80%, or higher than 80%. Average pore diameter of the mesh can range from about 300 µm to about 1,500 µm, from about 400 µm to about 1,000 µm, from about 500 µm to about 700 µm, or approximately 600 µm. Providing porous endplates can help ingrowth of bone through the cage 20 and allow faster and more complete spinal fusion.

In some embodiments, one or more portions of the external surface 21 of the cage 20 can include an increased roughness to retain the implant within the body of the patient. For example, the mesh or lattice structure 32 can protrude from the surfaces of the upper and lower endplates 22, 24 to grasp adjacent bone contacting surfaces. The mesh 32 can increase roughness of the upper and lower endplates 22, 24 along various contact surfaces to promote fixation of the implant when disposed within the body within the body of the patient. The increased roughness can increase a coefficient of friction of the cage 20 with respect to contact surfaces of adjacent vertebral levels to avoid migration of the cage 20 once disposed within the body. Frictional coefficients of the mesh can vary (e.g., based on the base material), though in some embodiments the frictional coefficient can be 1.0 or greater, 1.1 or greater, 1.2 or greater, and so forth.

Figure 8:
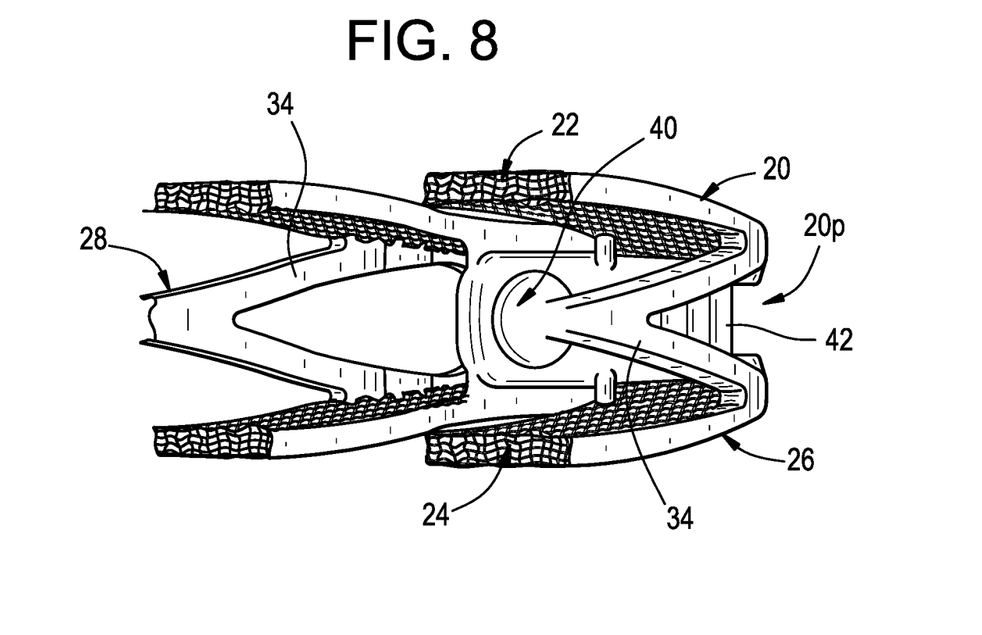
FIG. 8 is a perspective cross-sectional view of a proximal end of the cage of FIG. 1.

Alternatively, or in addition to the mesh 32, one or more the surfaces of the cage can include a plurality of ridges along the external surface of the cage, as discussed below with respect to FIG. 8. The ridges can take a variety of forms, however, in one embodiment, one or more of the upper endplate and/or the mesh can include teeth that lie along the external surface of the cage. In some embodiments, the teeth can further include a directional slant that can allow insertion of the cage but resist removal. The teeth can be configured to grasp adjacent bony surfaces to secure the cage within the body. Other surface features known to those skilled in the art can also be provided without departing from the spirit of the invention.

The distal end 20d of the cage 20 can be configured for insertion between vertebral bodies of a subject and to optimize stable fixation of the subject's vertebrae. As shown in FIGS. 4A-4B, the distal end 20d can have a rounded or bullet shape. Generally, the distal end 20d serves as the leading edge of the cage 20 when disposing the cage 20 through an incision and into an intervertebral implantation site. In some embodiments, the distal end 20d can have a narrower profile than a medial portion 20m of the cage to further facilitate insertion of the cage into the body, as shown in FIG. 4B. The proximal end 20p of the cage 20, on the other hand, is the trailing end of the spinal implant 10 and can include features adapted for anchoring the implant to a vertebral body, such as a plate member, as discussed further below. Plate members can have a variety of configurations. Non-limiting examples of configurations of plate members that can be used in accordance with the present invention are provided in FIGS. 9-13, and described in greater detail below. In some embodiments, the proximal end 20p can also include one or more features that can enable the implant to be mated to an insertion instrument. The proximal end 20p can have a profile that is of a similar size as the distal end 20d, though, in some embodiments, the proximal end can be sized larger than either of the distal end 20d and/or the medial portion 20m.

Figure 5:
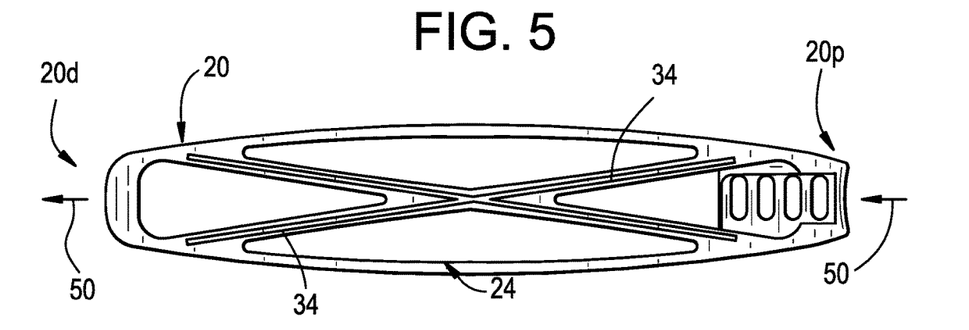
FIG. 5 is a side view of the cage of FIG. 1 showing an impaction force acting thereon.

FIG. 5 provides additional details about the anterior and posterior walls 26, 28 of the cage 20. In some embodiments, the anterior and posterior walls 26, 28 can include a connection between the upper and lower endplates 22, 24 to transmit forces during insertion. As shown, the connection can be in the form of struts 34 that form an X-shaped connection that can bear a load during cage impaction. When an impaction force acts on the cage 20 in the direction shown by arrows 50, for example, the struts 34 can absorb the impact and prevent plastic deformation of the cage. Indeed, in some embodiments the struts 34 can elastically deform to absorb impacts while maintaining their structural integrity to bear the load exerted by the force.

The cage 20 having X-shaped struts 34 can be additively manufactured to change a wall thickness of the struts 34 used in making the anterior and posterior walls. For example, by changing a thickness of the struts 34, the cage 20 can transmit insertion forces and/or adjust the elasticity thereof. In some embodiments, the cage 20 can have one or more connectors 36 disposed between the upper and lower endplates 22, 24 to further optimize elasticity of the cage 20. The struts and connectors can have varying thicknesses based on requirements for elasticity, load-bearing capability, etc. In some embodiments, the connectors 36 can include solid and/or hollow pillars that can be placed between the walls and/or endplates of the implant to help maintain the structural integrity of the implant. The connectors 36 can be placed between the X-shaped connection in the anterior or posterior walls 26, 28 and the upper endplate 22 as shown, though, in some embodiments, the connectors 36 can be positioned between the upper endplate 22 and the lower endplate 24 or the anterior or posterior walls 26, 28 and the lower endplate 24. In some embodiments, the connectors 36 can include a porous structure to allow the bone growth-promoting material to pass therethrough to further secure the cage 20 within the body. That is, in some embodiments the connectors 36 can be formed of a porous material, similar to the above-described mesh 32. Additionally or alternatively, the connectors 36 can be formed in shapes, such as a hollow cylinder, that provide an inner lumen that can receive bone ingrowth and/or osteointegration promoting materials. Still further, in some embodiments one or more of the struts 34, or one or more portions of one or more of the struts, can be similarly constructed.

Figure 6:
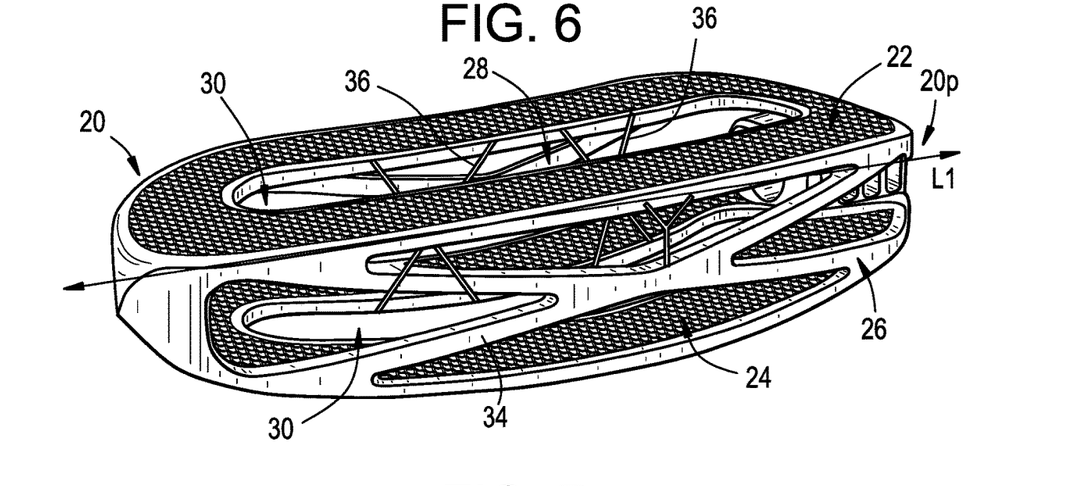
FIG. 6 is a perspective view of the cage of FIG. 1 having connectors disposed between the upper and lower endplates.
Figure 7:
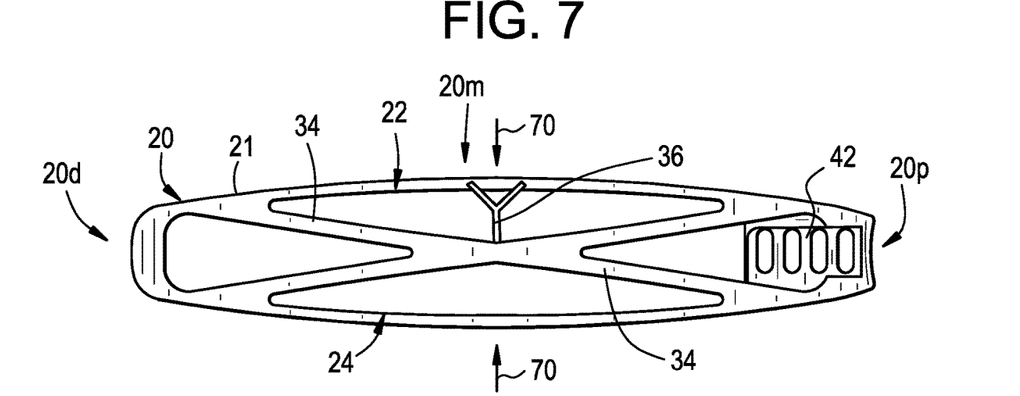
FIG. 7 is a side view of the cage of FIG. 1 having the connector extending from the upper endplate.

As shown in FIG. 6, the connectors can be placed throughout the cage 20 to distribute loads evenly. The positioning of the connectors 36 throughout the cage 20 can be used adjust one or more of strength, deflectability, and/or flexibility of the cage 20. For example, one or more of the connectors 36 can be positioned between the anterior wall 26 and the upper endplate 22, as shown in FIG. 7, to optimize elasticity of the cage 20 and enable post-operative load transmission in the face of anatomical loads, as shown by the arrows 70. In some embodiments, the connectors 36 can be positioned along a perimeter of the cage 20, or alternatively, at the medial portion 20m of the cage 20, as shown in FIG. 7, to serve as a connection between the porous endplate 22 and the external surface 21 to allow migration of bone growth promoting materials.

Figure 14:
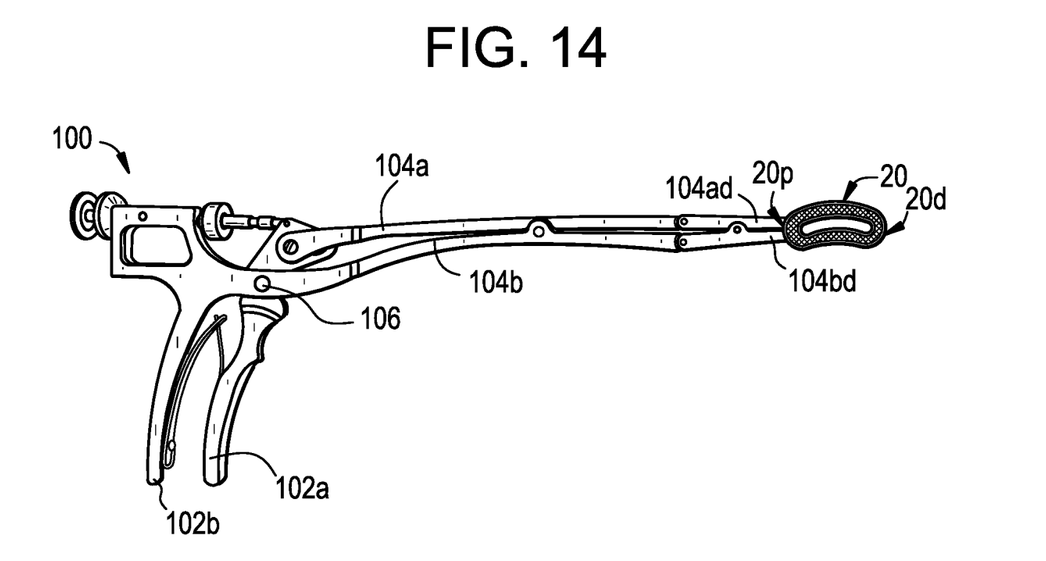
FIG. 14 is a perspective view of an insertion instrument attached to the cage of FIG. 1.
Figure 15:
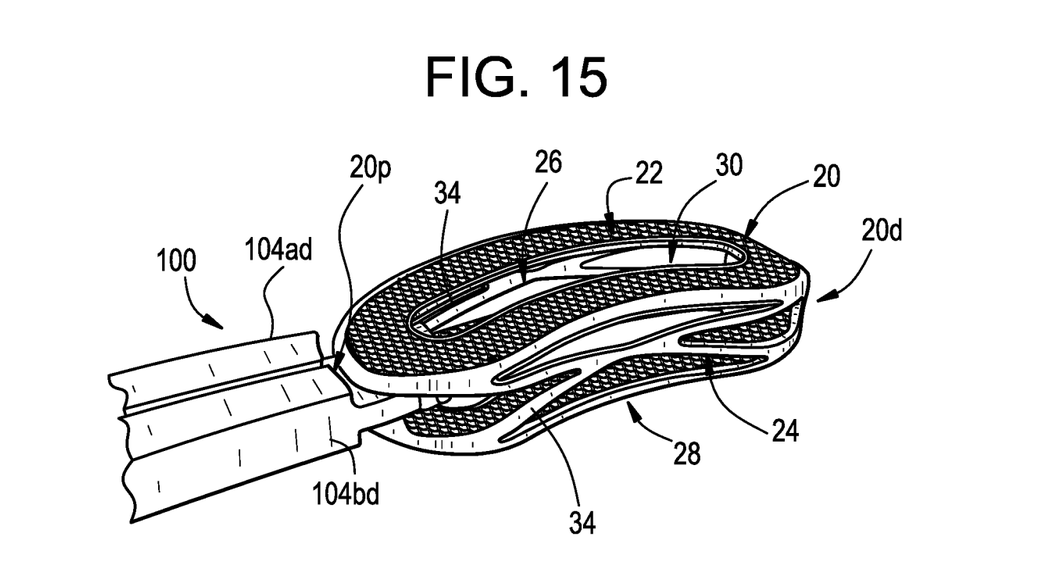
FIG. 15 is a magnified perspective view of the insertion instrument of FIG. 14 connected to the proximal end of the cage of FIG. 1.

The proximal end 20p of the cage 20 can have one or more features that enable the cage to be mated to an insertion instrument 100 (as discussed in greater detail in FIGS. 14-15). For example, the proximal end 20p can include an orifice or recess 40 that is configured to receive one or more devices therethrough. As shown in FIG. 8, the orifice 40 can extend from the proximal end into an interior portion of the cage 20 to allow access to an interior volume of the cage for delivery of, for example, bone-growth promoting material, cement, etc. The orifice 40 can extend at an angle with respect to the longitudinal axis L1 of the cage, though, in some embodiments, the orifice 40 can extend parallel to the longitudinal axis L1. One or more of an inserter device, a bone graft delivery tool, or other devices for manipulating the cage 20 can be inserted through the orifice 40. In some embodiments, the orifice 40 can include a threaded connection (not shown) to secure the devices within the orifice 40.

A sidewall of the proximal portion of the cage 20 surrounding the orifice 40 can include a series of ratchets, steps, protrusions, recesses, or other features 42 extending along an outer surface thereof. The ratchets 42 can allow an inserter device 100 or a clamp (not shown) to couple to the cage 20. The inserter device 100 can secure to one or more of the ratchets 42 to set a fixed distance between the inserter device 100 and the cage 20. In some embodiments, the orifice 40 can include a clamp (not shown) attached on an outer surface thereof to strengthen the fixation of the inserter device 100 to the cage 20.

Figure 9:
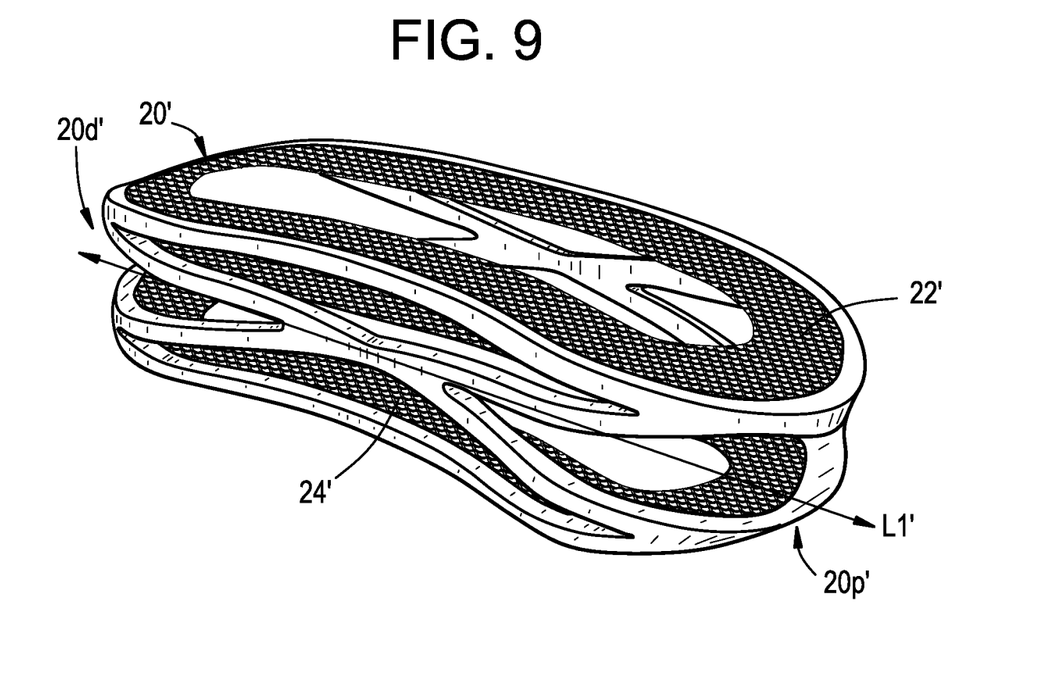
FIG. 9 is a perspective view of another embodiment of a spinal implant.
Figure 10:
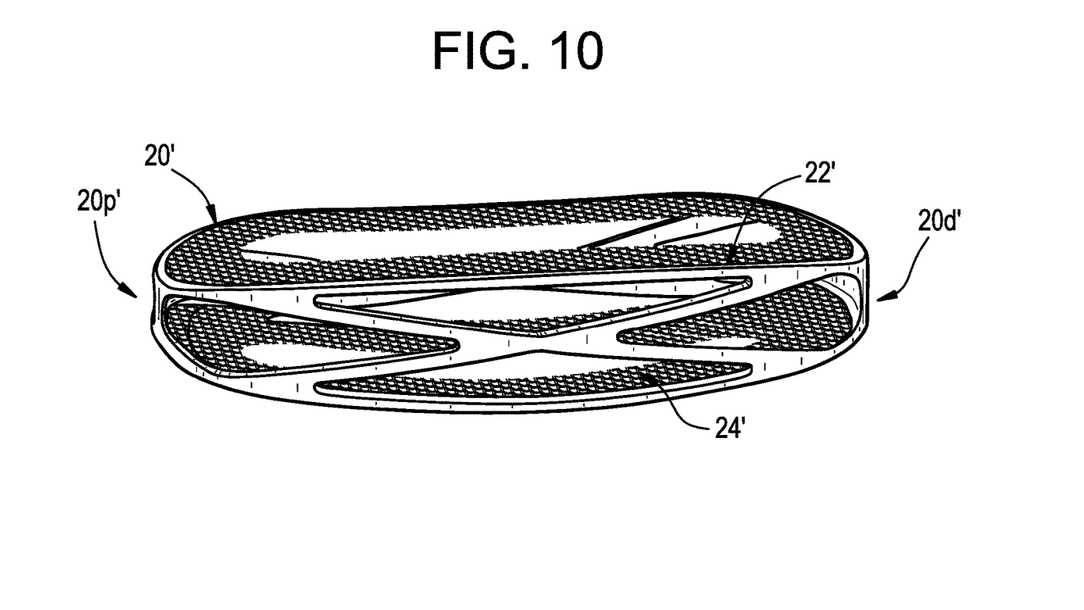
FIG. 10 is a perspective front view of the cage of FIG. 9.

FIGS. 9 and 10 illustrate an alternate embodiment of a cage 20'. The external surface 21' of the cage 20' is generally similar to the cage 20, although as shown the cage 20' does not have an orifice extending therethrough. In such embodiments, the inserter device 100 can grasp the upper and lower endplates 22', 24' for inserting the cage 20' into the body. Alternatively, in some embodiments, the inserter device 100 can extend between the upper and lower endplates 22', 24' of the cage 20' to grasp one or more of the proximal end 20p' and/or distal end 20d' to couple to the cage. Once the inserter device 100 is coupled thereto, the cage 20' can be positioned at a desired location within the body.

Figure 11:
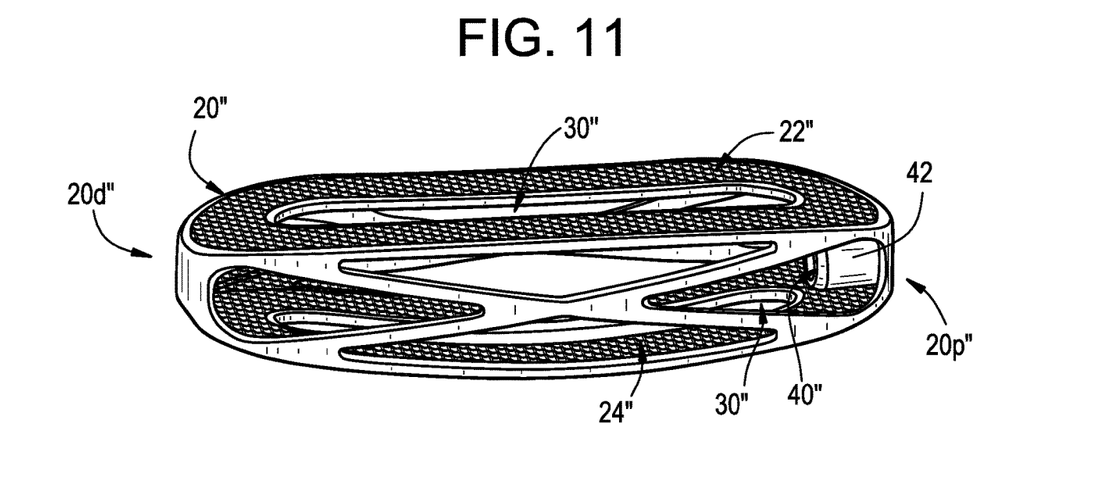
FIG. 11 is a schematic front view of another embodiment of a spinal implant.

Yet another embodiment of a cage 20" is illustrated in FIG. 11. The cage 20" of FIG. 11 is similar to the cage of FIGS. 1-8 because the cage 20" has an orifice 40" at its proximal end 20p" for receiving the inserter device therethrough. While the orifice 40" of the cage 20" extends from the proximal end 20p" into an interior portion of the cage, the orifice 40" does not have ratchets or other features formed on an outer surface surrounding the orifice. Rather, as shown, the orifice 40" is defined by a smooth outer surface 42 that extends into the interior of the cage 20" and terminates prior to openings 30" in the upper and lower endplates 22", 24".

In some embodiments, the implant 10 can include both a cage that is configured to be inserted between adjacent vertebrae and a plate member 50 that can be appended to, or integrally formed with, the cage and that can be used to assist in securing the implant 10 at a desired location, such as with respect to a lateral wall of one or more vertebral bodies. As illustrated and discussed above, the cage 20 can be generally oriented in a transverse plane of the body when implanted in some embodiments, and in such an orientation would extend laterally to medially between its proximal and distal ends 20p, 20d. An appended plate member 50, when implanted, generally extends in the caudal to cephalad direction, though alternate orientations of the plate member with respect to the cage is possible. Not all embodiments include a plate member 50, e.g., the previously discussed embodiments of the cage 20, 20', 20" illustrate implants that do not include a plate member (though one could be coupled to the cage 20 using, for example, the ratchets or other features 42 formed thereon). Although a plate member 50 can assist in securing the implant at a desired location between vertebral bodies, the shape of the implant itself can sufficiently secure placement of the implant in some embodiments. For example, the banana-like shape and asymmetrical curve of the cage 20, 20', 20", along with other features such as surface protrusions, roughened surfaces, etc., can enable stable placement without using a plate member 50.

Figure 12:
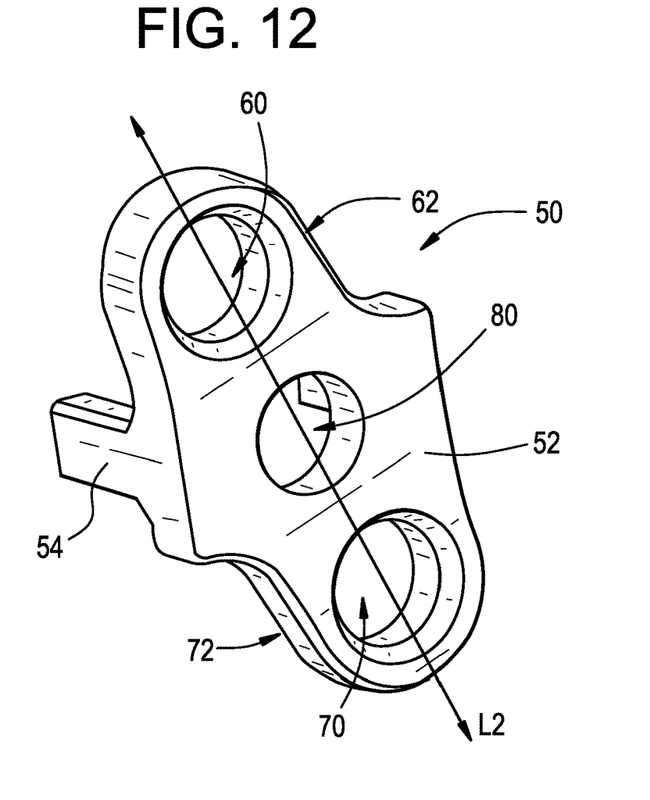
FIG. 12 is a perspective view of an embodiment of a plate member that can attach to spinal implant.

FIG. 12 illustrates an exemplary embodiment of a plate member 50. The plate member 50 can include an elongate body 52. The body 52 can extend along a long axis $L_2$ that is substantially perpendicular to a coupling portion 54 to allow the plate member 50 to couple to adjacent vertebral bodies along an axis that is substantially perpendicular to a longitudinal axis of a cage extending between vertebral bodies (e.g., axis L1''' of FIG. 13). The body 52 can include one or more mating features to assist in mating the plate member 50 to vertebrae. As shown, the mating features can include a first bore 60 in a first wing 62 of the plate member 50 and a second bore 70 in a second wing 72 of the plate member 50. Anchor members, such as screws or nails that are complementary to the bores 60, 70 can be used to secure the plate member 50, and thus the spinal implant 10. The plate 50 can also include a central bore 80 that is configured to be engaged by an insertion instrument to assist in insertion of the implant or to allow an instrument to pass therethrough into an interior volume of a cage coupled to the plate 50. In some embodiments, one or more of the bores can be threaded (not shown).

In some embodiments the plate member 50 can include one or more anti-migration features. For example, one or more spikes, ridges, hooks, or other bone-engaging features can be disposed on an internal surface of the plate member 50. These features can be configured to engage an adjacent vertebral body to assist in maintaining the plate, and thereby the implant, at a desired location.

The plate member 50 can have a variety of shapes and sizes. For example, the plate member 50 can be generally rectangular or oval shaped and can extend away from the upper endplate 22 and the lower endplate 24 of the cage along an axis L2 that is substantially perpendicular to the axis of the cage L1''' shown in FIG. 13. Alternatively, it can extend in a single direction (e.g., to only one side of the cage) such that it mates to only one of the two adjacent vertebral bodies.

The plate member 50 can further include a coupling member 54. The coupling member 54 can be used to append the plate member 50 to the cage 20. For example, the coupling member 54 can be received in the proximal end 20 of the cage 20 to couple the plate member to the cage 20. As shown, the coupling member 54 can extend from an interior surface (not visible) to be received within the cage. The coupling member 54 can be in the form of an extension, as shown, though the coupling member can be in the form of a hook or an snap-fitting member configured to be received in the orifice of the cage 20 in other embodiments.

Figure 13:
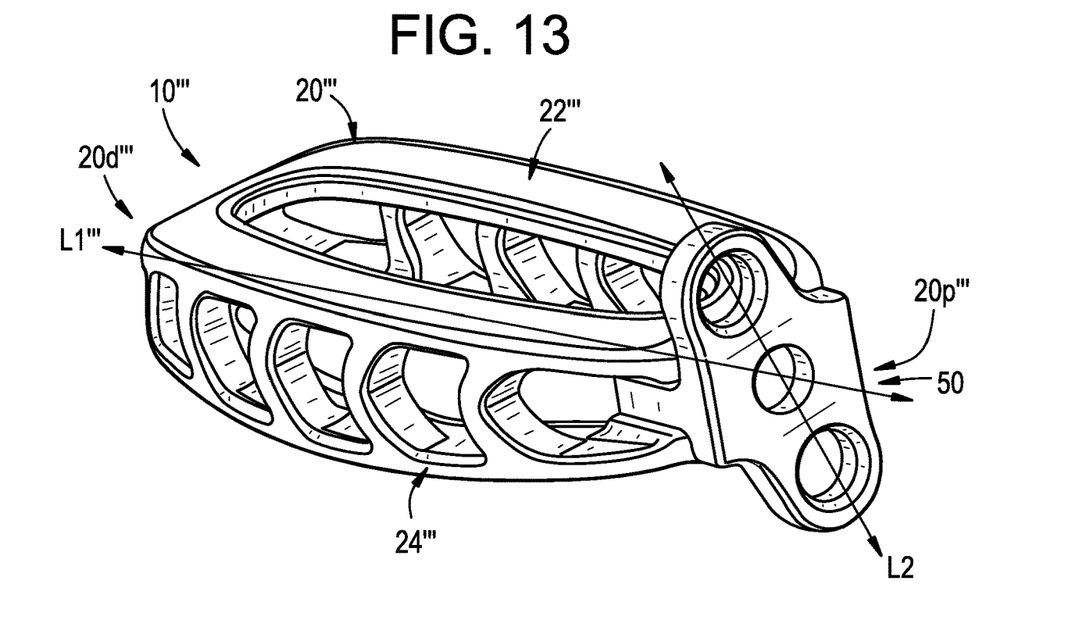
FIG. 13 is an embodiment of a spinal implant that includes the plate member of FIG. 12 attached to a cage.

FIG. 13 illustrates an implant 10''' that includes the plate member 50 disposed in proximity to the proximal end 20p''' of a cage 20'''. While in the illustrated embodiment the plate member 50 is appended to the proximal end 20p''', it can be formed integrally with the proximal end or appended to the proximal end 20p''' in other ways known to those having skill in the art. By way of non-limiting examples, a plate member can be slidingly coupled to a cage or removably and replaceably coupled to a cage.

As shown, the coupling member 54 can be received in the proximal end 20p''' of the cage 20''' such that the central bore 80 of the plate 50 aligns with a longitudinal axis L1''' of the cage 20'''. For cages having an orifice, the central bore 80 can be received and/or otherwise align with the orifice such that an inserter device can be inserted through the central bore 80 and the orifice into an interior of the implant. Bone graft or bone growth-promoting material can be incorporated into the cage through the central bore 80 and the orifice 40 before, during, or after insertion is complete.

The plate member 50 generally extends in a direction that is opposite to that of the elongate direction of the cage 20'''. As shown in FIG. 13, while the cage 20''' extends along a longitudinal axis $L_1'''$, the plate member 50 extends in a long axis $L_2$ in a direction that is at an oblique or non-parallel angle with respect to the direction of the longitudinal axis $L_1'''$. In some embodiments, the plate member 50 can be oriented such that the plate member 50 extends at an angle that is generally perpendicular with respect to the longitudinal axis $L_1'''$.

While the illustrated embodiment shows the plate member 50 being disposed symmetrically with respect to the cage 20''', in some embodiments, the plate member 50 can also be asymmetric about an axis of the cage such that the plate member 50 is not equally disposed on both sides of an axis of the cage 20'''. For example, as shown in FIG. 13, the plate member 50 can be positioned such that the wings 62, 72 of the plate member 50 are offset in opposite directions from one another. And, in other embodiments, as described above, the plate member 50 can include only one of the wings 62, 72, such that the plate member 50 is coupled to only one vertebra adjacent to the cage 20''', not both.

In a method of implanting the cage 20, an incision or delivery aperture can be formed in an area near the spine. In an exemplary embodiment, the incision can be formed in accordance with a lateral or posterior-lateral spinal surgery approach, though it will be appreciated that the cage design concept can be transferred to ALIF, TLIF, lateral, and/or cervical applications, with the location of the incision varying based on the cage and delivery point being used.

After the incision is formed, and after any desired or necessary preparation of the space between the vertebrae, an implant can be inserted through the incision and to a desired implant location. Alternatively, an access port can be inserted into the incision to form a channel and the implant can be inserted therethrough and placed at a desired implant location. In one exemplary embodiment, and as shown in the above figures, the cage can be configured to be inserted into the lumbar region of the spine, preferably between any two of the vertebrae in the L1 through L5 region. In another exemplary embodiment, the desired implant location is in the cervical region of the spine, preferably between any two of the vertebrae in the C3 through C7 region. For example in some embodiments the cage can be configured to be disposed between the C4 and C5 vertebrae. The distal end of the cage can first be inserted into the space between the desired vertebrae, and then the implant can be rotated to the desired implant location. In some embodiments, the cage can fill greater than about one-third of the footprint of a vertebral body and, in certain embodiments, can fill between about one third and about two thirds of the footprint of a vertebral body. Further, in certain embodiments, such as anterior lumbar interbody fusion (ALIF) or lateral spine surgery techniques, cages can be utilized that fill greater than about two thirds of the footprint of a vertebral body.

As explained above, the implant can be additively manufactured to match the contours of the desired implant location. Such matching can be achieved by, for example, scanning a patient's anatomy using any of a variety of surgical imaging techniques (e.g., CT, MRI, etc.) either during or before a procedure. In some cases, the additive manufacturing process can be used to create the desired implant in a short period of time before or even during a procedure after imaging is complete. Accordingly, in one exemplary embodiment the upper and lower endplates 22, 24 can be configured to substantially match the anatomy of adjacent vertebral bodies such that the implant 10 can be implanted in a position that supports adjacent vertebral bodies. In other embodiments the anterior wall 26 of the cage 20 or the posterior wall 28 of the cage 20 can be substantially aligned with the curve of the anterior portions of the vertebrae. In still other embodiments, the implant 10 can be implanted at an angle with respect to a spine. One skilled in the art will recognize that the angle can be created during the act of inserting the implant through the incision, or any time thereafter, including at the site of the vertebral bodies.

As discussed above, the implant can be coupled to an inserter device 100 to be positioned between adjacent vertebral bodies. An exemplary embodiment of an inserter device 100 is shown in FIG. 14. The inserter device 100 can include a pair of handle portions 102a, 102b each connected to an elongate body 104a, 104b, respectively. The elongate bodies 104a, 104b can couple to one another at one or more hinged portions 106 as shown. The hinged portion 106 can allow the elongate bodies 104a, 104b to pivot relative to one another in a manner similar to scissors to clamp an object, e.g., the cage 20, between distal ends 104ad, 104bd of the elongate bodies 104a, 104b. For example, movement of the handle portions 102a, 102b relative to one another can cause a distance between the distal ends 104ad, 104bd of the elongate bodies to increase or decrease. By moving the handle portions 102a, 102b closer to one another, as shown in FIG. 15, the elongate bodies 104a, 104b can move closer to one another, thereby clamping onto the cage 20. Alternatively, the distal ends 104ad, 104bd can engage the one or more sets of ratchets or other features 42 on the outer surface of the orifice 40 to clamp the inserter device 100 to the cage 20. The presence of multiple ratchets or other features 42 can allow a user to preset a distance between the elongate bodies 104a, 104b and the cage for regulating the insertion of the cage 20 into the patient.

The inserter device 100 can clamp to the proximal end 20p of the cage 20. In some embodiments, the inserter device 100 can be configured to be received in the orifice 40 of the cage to couple with the cage. In such embodiments, the distal ends 104ad, 104bd of the elongate bodies 104a, 104b can move closer to one another such that a width of the distal ends 104ad, 104bd is narrower than a diameter of the orifice, thereby allowing the distal ends 104*ad*, 104*bd* to be received within the orifice. The handle portions 102*a*, 102*b* can then be moved apart to engage an inner surface of the orifice 40 to secure the inserter device 100 to the cage 20.

Although the implants discussed herein are generally illustrated and discussed with respect to being used in a lumbar region of a spine, the implants can also be used in other regions of the spine, such as the thoracic and cervical regions, as well as in other skeletal structures of a subject, such as skulls, femurs, tibias, and hips. Likewise, although the implantation technique is generally described as being a lateral approach, the implants disclosed herein can be used in other approaches and in other locations in a subject.

One skilled in the art will appreciate further features and advantages of the invention based on the above-described embodiments. Accordingly, the invention is not to be limited by what has been particularly shown and described, except as indicated by the appended claims. A person skilled in the art will be able to apply features disclosed in one implant and generally apply those features to other implants as well because many of the features described herein are capable of being mixed and matched across various embodiments. All publications and references cited herein are expressly incorporated herein by reference in their entirety.

The invention claimed is:

1. A spinal implant, comprising:
   an upper plate;
   a lower plate;
   a tapered end extending between the upper plate and the lower plate that is configured for insertion into intervertebral space;
   a second end opposite the tapered end;
   a plurality of struts extending laterally between the tapered end and the second end; and
   one or more connectors disposed either between the upper plate and one or more of the plurality of struts, or between the lower plate and one or more of the plurality of struts, the one or more connectors including a cylindrical shape having an inner lumen that receives bone ingrowth or osteointegration promoting materials therethrough.

2. The implant of claim 1, further comprising a connector extending between the upper plate and the lower plate.

3. The implant of claim 2, wherein the connector is disposed within an interior volume defined by the implant.

4. The implant of claim 1, wherein the one or more connectors are formed along a perimeter wall of the implant.

5. The implant of claim 1, wherein the one or more connectors are configured to support loads applied to the upper end plate and the lower end plate.

6. The implant of claim 1, wherein the one or more connectors are formed of a porous mesh.

7. The implant of claim 1, wherein at least a portion of the implant is formed of a porous mesh configured to promote osteointegration.

8. The implant of claim 7, wherein the portion of the implant is formed of any of titanium, polyetherketoneketone (PEKK), a ceramic, and a nickel titanium alloy.

9. The implant of claim 1, wherein any of the upper plate and the lower plate are curved such that a distance between the upper plate and the lower plate varies along the implant.

10. The implant of claim 1, wherein at least one of the upper plate and the lower plate include a roughened surface configured to promote bone fusion.

11. The implant of claim 1, wherein the implant is formed of a porous titanium mesh having reduced stiffness and increased radiolucency compared to solid titanium.

12. The implant of claim 1, wherein at least two of the plurality of struts cross to form an X-shaped connection extending along a sidewall of the implant between the upper plate, lower plate, tapered end, and second end.

13. The implant of claim 1, wherein at least one of the upper plate and lower plate includes one or more surface features configured to prevent migration of the implant.

14. The implant of claim 1, wherein an orifice is formed in the second end of the implant.

15. The implant of claim 14, further comprising a plate coupled to the second end of the implant, the plate including a plurality of through-holes.

16. The implant of claim 15, wherein one of the plurality of through-holes in the plate aligns with the orifice formed in the second end of the implant.

17. The implant of claim 15, wherein one of the plurality of through-holes is disposed any of above the upper plate and below the lower plate.

18. The implant of claim 15, wherein the plate couples to the implant by interfacing with surface features formed on first and second sidewalls of the second end of the implant that are disposed on opposite sides of the orifice.

19. The implant of claim 14, further comprising a plate integrally formed with the second end of the implant, the plate including a plurality of through-holes.

20. The implant of claim 1, wherein a first terminal end of the one or more connectors abuts the upper plate and a second terminal end of the one or more connectors abuts one or more of the plurality of struts or a first terminal end of the one or more connectors abuts the lower plate and a second terminal end of the one or more connectors abuts one or more of the plurality of struts.

* * * * *